United States Patent [19]

DeMane et al.

[11] Patent Number: 5,336,163
[45] Date of Patent: Aug. 9, 1994

[54] EXPANDABLE NASAL STENT

[75] Inventors: Catherine DeMane; Robert Schwarz, both of Memphis, Tenn.

[73] Assignee: Smith & Nephew Richards, Inc., Memphis, Tenn.

[21] Appl. No.: 1,064

[22] Filed: Jan. 6, 1993

[51] Int. Cl.$^5$ ............................................. A61F 13/00
[52] U.S. Cl. ........................................ 602/46; 604/11;
606/191; 606/192; 606/196; 606/199
[58] Field of Search ............................ 128/858, 206.11;
602/42, 46, 74; 604/11, 381, 307, 304; 606/23.2,
191, 192, 196, 199

[56] References Cited

U.S. PATENT DOCUMENTS

| | | | |
|---|---|---|---|
| 3,416,524 | 12/1968 | Meier | 604/304 |
| 3,849,238 | 11/1974 | Gould et al. | 602/46 |
| 3,978,855 | 9/1976 | McRae et al. | 602/46 |
| 4,030,504 | 6/1977 | Doyle | 606/199 |
| 4,233,969 | 11/1980 | Lock et al. | 602/46 |
| 4,338,941 | 7/1982 | Payton | 606/196 |
| 4,646,739 | 3/1987 | Doyle | 606/192 |
| 4,950,280 | 8/1990 | Brennan | 606/196 |
| 4,994,047 | 2/1991 | Walker et al. | 604/264 |
| 5,065,752 | 11/1991 | Sessions et al. | 602/46 |
| 5,094,233 | 3/1992 | Brennan | 602/17 |

Primary Examiner—C. Fred Rosenbaum
Assistant Examiner—N. Kent Gring
Attorney, Agent, or Firm—Pravel, Hewitt, Kimball & Krieger

[57] ABSTRACT

An expandable nasal stent for postoperative nasal packing is formed of a body with outer surfaces that correspond generally to the surfaces that define a human nasal cavity. The body is formed of a highly porous, pliable and absorbent foam material having a nonadherent, minimally porous outer surface.

10 Claims, 3 Drawing Sheets

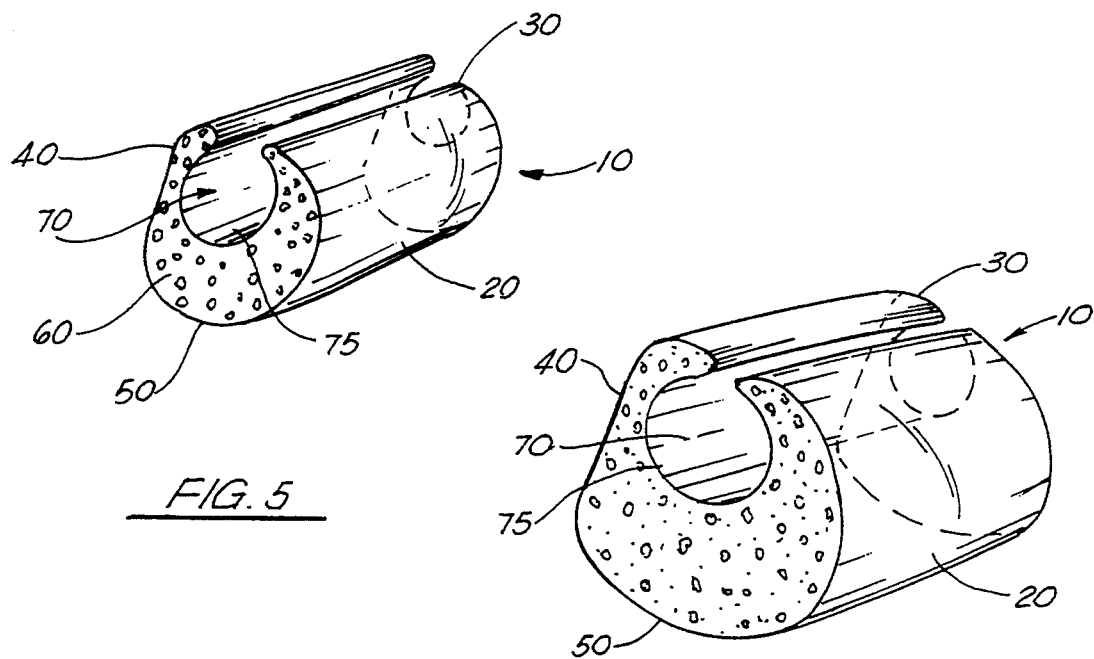
FIG. 5
FIG. 6
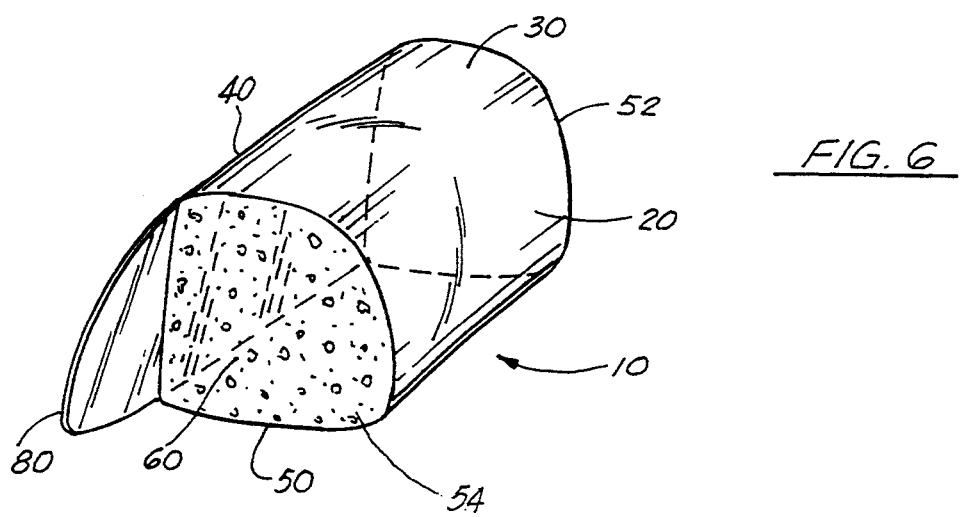
FIG. 7
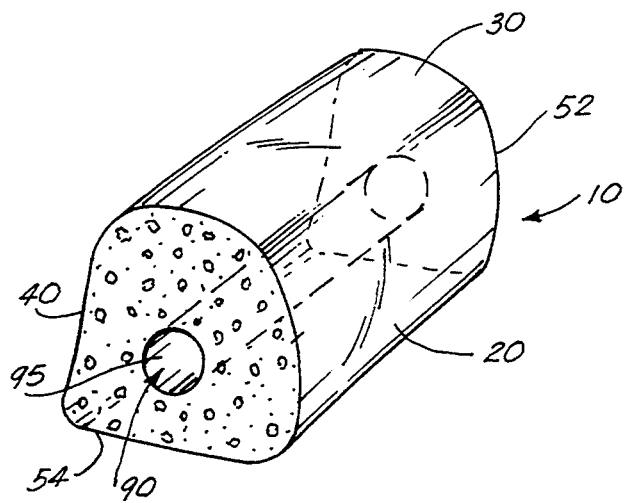
FIG. 8

EXPANDABLE NASAL STENT

FIELD OF THE INVENTION

The present invention relates to a nasal stent for postoperative nasal packing and, more particularly, to a stent which is formed of a material that does not adhere to the mucosal surfaces of the nasal cavity and which expands into contact with the mucosal surfaces for the prevention of adhesion and scar formation.

BACKGROUND OF THE INVENTION

Surgery of the nasal cavity and paranasal sinuses often results in the mucosal lining of the nasal cavity becoming raw and rough. These surfaces have a tendency to adhere to each other in the immediate postoperative period and form scars. This is of particular concern in the superior portion of the nasal cavity where mucosal surfaces are close to each other. Such adhesions and scars cause postsurgical complications such as decreased air flow and usually require surgical correction.

The most common approach to the prevention of adhesions or scars is to pack the nasal cavity with lubricated gauze strips or other materials such as telfa pads. Surgeons also pack the operative site with hydratable and expandable packing or other materials such as prefabricated tampons. However, these approaches are specifically designed for the control of hemostasis, and not the prevention of scar formation.

One such device is described in U.S. Pat. No. 4,646,739 to Doyle where a sinus pack tampon is used as hemostat for short term packing of the operative site. The tampon is formed of a compressed porous material, such as a dry hydrocellulose, that expands on contact with fluid, to prevent nasal hemorrhaging. The tampon is shaped to conform to the nasal passage and prevent apparition into the nasal fossa.

Another postoperative packing known as "Merocel Sinus-Pak", is formed of an open cell foam of polyvinyl alcohol. This product, however, dries out rapidly and allows tissue to grow into the open cells of the foam.

In addition, such packings tend to displace the middle turbinate causing it to adhere to the nasal septum, with resultant airway obstruction. While various septal splints have been used to prevent adhesions to the nasal septum, adhesions of the lateral side of the middle turbinate or concha to the upper sinus wall are not prevented.

A device designed to prevent adhesions and scar formation between the middle turbinate and lateral nasal wall or septum is described in U.S. Pat. No. 5,094,233 to Brennan, entitled "Turbinate Sheath Device." A septal splint and solid plastic sheath surround the middle turbinate. However, the sheath does not expand to line the mucosal surfaces of the nasal cavity, nor does it apply pressure to the medial and lateral aspects of the nasal cavity for reducing postoperative edema and aid in mucosal healing.

U.S. Pat. No. 4,030,504 to Doyle, entitled "Nasal Hemostat and Methods of Construction of Nasal Hemostat," describes a nasal tampon fabricated from an absorbable, expandable foam to control postoperative bleeding. However, the porous material of the nasal hemostat does not prevent adhesion of the tampon surface to the nasal mucosa. Additionally, the nasal hemostat does not expand to conform to surfaces of the nasal mucosa, nor does it expand into the superior portion of the nasal cavity.

SUMMARY OF THE INVENTION

The subject invention solves the problems discussed above by providing a nasal stent that is designed to conform to the shape of the nasal cavity by expanding upon contact with fluid to engage the mucosal surfaces of the nasal cavity for preventing postoperative scar formation between the mucosal surfaces. The outer surface of the stent is formed of a nonadherent, minimally porous material that allows for normal mucosal healing and does not adhere to the mucosa.

The stent reduces postoperative swelling by applying light, even pressure to the mucosal surfaces and absorbing fluids and blood which may be present in the nasal cavity. The stent is shaped anatomically to conform in all dimensions to the nasal cavity. The stent is small in its pre-swollen state and expands on contact with fluid to fill the nasal cavity, particularly the superior portion.

The absorbency of the foam creates a moist environment in which the nasal mucosal can heal. The light, even pressure of the expanding foam against the medial and lateral aspects of the nasal cavity holds the stent in place. This pressure also serves to reduce postoperative edema which is a further aid in mucosal healing. The various configurations of the stent cover the anatomic variations found in the nasal cavity. One configuration is used when no middle turbinate or concha is present, while a second configuration incorporates a trough along the superior side to accommodate the middle turbinate.

BRIEF DESCRIPTION OF THE DRAWINGS

The objects, advantages and features of the invention will become more apparent when the detailed description of exemplary embodiments is considered in conjunction with the appended drawings, in which:

FIG. 5 is a perspective view of a second embodiment of the present invention with the stent in its unexpanded condition;

FIG. 6 is a perspective view of the stent of FIG. 5, with the stent in its expanded condition;

FIG. 7 is a perspective view of a third embodiment of the present invention; and FIG. 8 is a perspective view of a fourth embodiment of the present invention.

DETAILED DESCRIPTION OF A EXEMPLARY EMBODIMENTS

Figure 1:
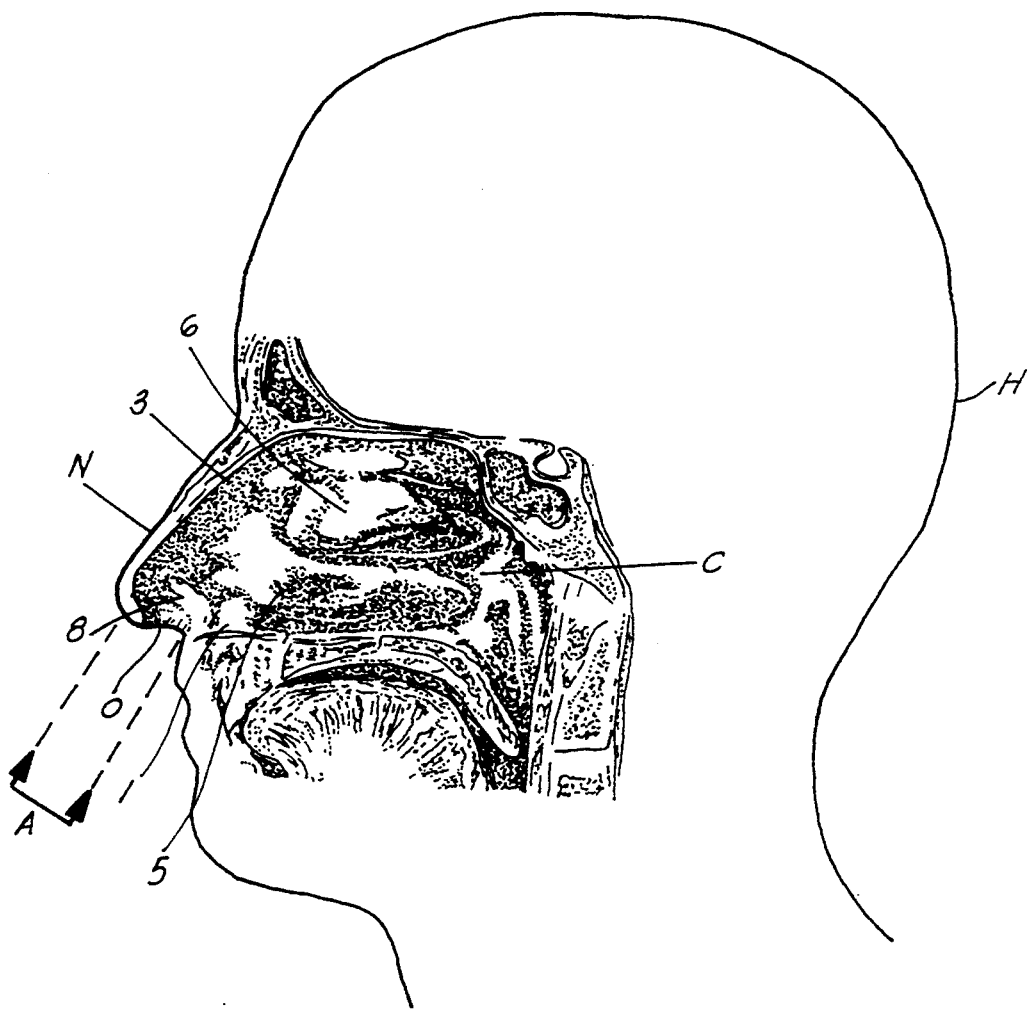
FIG. 1 is a schematic view of a human head showing the nasal cavity in cross-section.
Figure 2:
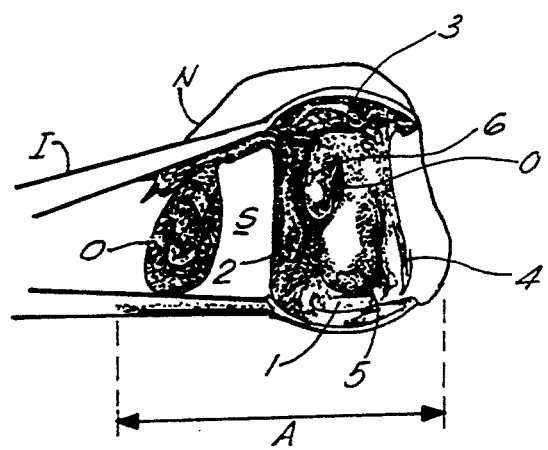
FIG. 2 is a frontal view of the nose looking along line A in FIG. 1, and showing one of the nostrils widened with a speculum.

Referring to FIGS. 1 and 2, reference letter H refers to a human head, and letter N to its nose which has two nostrils or openings O separated by a septum S (FIG. 2) that opens into an internal nasal cavity C. The nose N and nasal cavity C are part of a human's respiratory and olfactory systems and are instrumental in the exchange of heat and water vapor within the human body. As shown both in the cross-sectional view of FIG. 1 and the view of FIG. 2 looking into one of the nostrils O which has been expanded by using an instrument I known as a speculum, the anatomy of the nasal cavity includes a floor 1, a medial wall 2 which defines one side of the septum S, a roof 3 and a lateral wall 4. An inferior nasal turbinate 5 and a middle nasal turbinate 6 project from the lateral wall 4 and are responsible for the exchange of heat and water vapor in the nasal cavity C.

Figure 3:
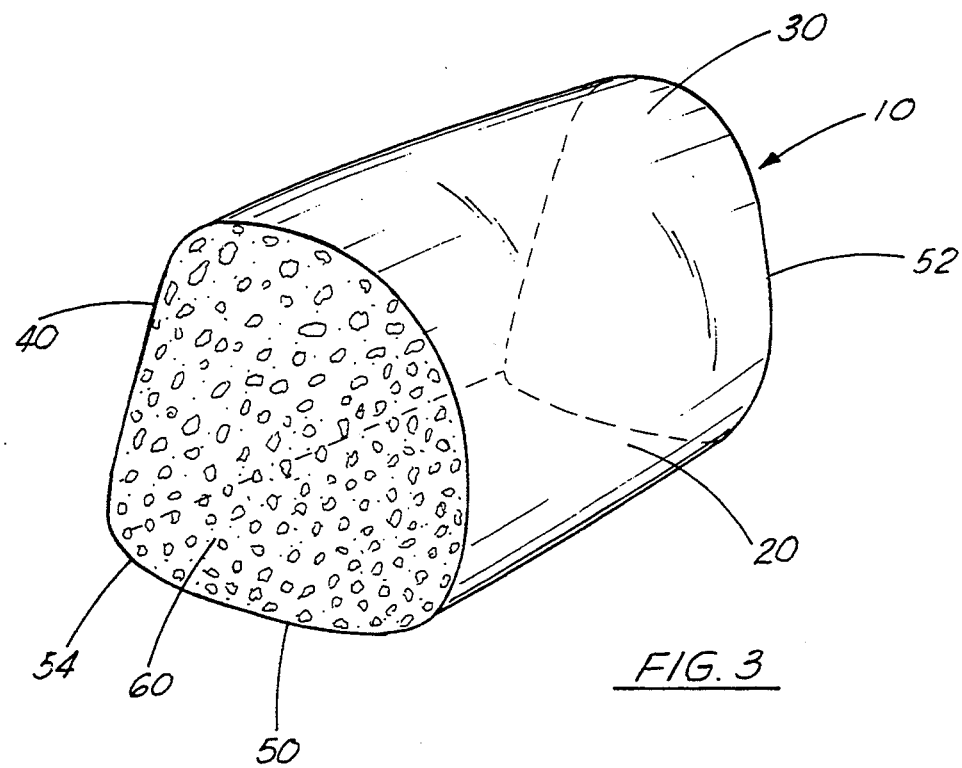
FIG. 3 is a perspective view of one embodiment of the expandable nasal stent of the present invention.

After surgery is performed in the nasal cavity or the adjacent paranasal sinuses (not shown) the mucosal surfaces that line the nasal cavity C tend to become raw and rough. This is prevented in accordance with the invention by inserting a stent 10 of the type shown in FIG. 3, which is shaped to conform generally to the nasal cavity and which is formed of an expandable foam material. The stent 10 has a basic shape which includes a lateral side surface 20 that is outwardly curved to correspond to the curvature of the lateral nasal wall 4 so that when the stent expands upon contact with body fluids, the surfaces that form the lateral wall 4 are engaged by the stent 10. A superior wall surface 30 is relatively narrow in width and is slightly curved to generally correspond to the shape of the roof 3 of the nasal cavity C. The stent 10 also has a medial side surface 40 that is substantially flat, corresponding to the structure of the medial wall 2. An inferior surface 50 of the stent 10 is substantially flat, corresponding to the floor 1 of the nasal cavity C. Opposing end surfaces 52, 54 are also substantially flat.

The stent 10 is formed of a medical grade polyurethane hydrophilic foam manufactured from a base material of polyether polyisocynate resin. This material is commercially available and has previously been used in wound dressing applications, for burn wounds, full thickness ulcers and pressure sores. The material can be formed with a cell structure of 5–200 cells/inch.

The internal portion 60 of the stent 10 is formed with a relatively high absorbency, toward the upper end of the range mentioned above. All the outer surface portions are formed of a material that is chemically identical to the internal portion 60, but which is a minimally porous layer of 0.001 mm./2 mm. thick. Since the outer surface portions are minimally porous, they are smooth and nonadherent to the mucosal tissue. This material has been found to be non-toxic and sterilizable and can be purchased from the manufacturer with various absorbencies and various skin thicknesses as described above.

Figure 4:
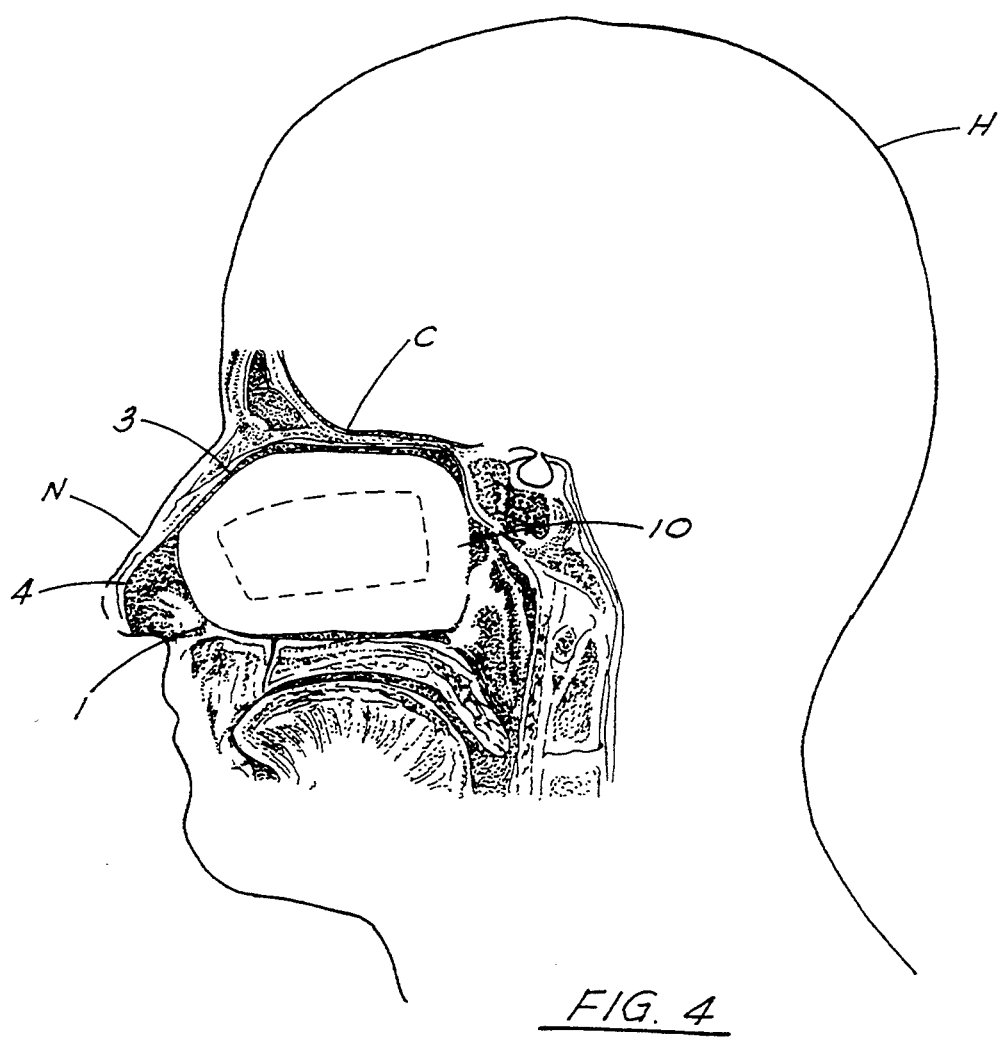
FIG. 4 is a schematic view of a human head similar to FIG. 1, with the stent of FIG. 3 inserted in the nasal cavity.

The stent 10, in its unexpanded condition, is dimensioned to be smaller than the nasal cavity so that it can easily be inserted postoperatively, as shown by the dotted lines, in FIG. 4. As the stent 10 absorbs moisture in the form of blood and other body fluid from the nasal cavity, it expands on contact with the fluid to fill the nasal cavity, particularly the anterior portion closer to the nostril O, as shown by the solid lines in FIG. 4. Upon expansion, the stent 10 engages and covers all the mucosal surfaces due to its anatomically correct shape. These smooth surfaces do not adhere to the healing mucosal tissue, with the absorbency of the foam creating a moist environment in which the tissue can heal. The stent 10 is held in place by the gentle, even pressure of the foam material which has expanded against the surfaces of the nasal cavity, which tends to reduce postoperative edema and aid in mucosal healing.

FIG. 5 shows an alternative embodiment of the stent 10 where a trough 70 is formed along the superior wall surface 30 in order to accommodate the middle nasal turbinate 6. The outer surface of the trough 70 is minimally porous, as are the other external surfaces of the stent 10 discussed above. This environment is designed for use in cases where the middle nasal turbinate 6 is substantially large, to the extent that it would prevent accurate placement of the stent shown in FIG. 3. FIG. 6 shows the stent of FIG. 5 after it has been expanded through the absorption of moisture, illustrating in particular that the trough 70 undergoes minimal expansion while the remainder of the stent 10 expands as described above.

Another alternative embodiment is shown in FIG. 6, where the stent 10 has a thickened medial surface 40 that is reinforced by a mechanically strong, non-porous thickened portion 80, about 2 mm thick, in order to form a splint. This splinting portion 80 is formed as an integral part of the stent 10, of a material which is chemically identical to the remainder of the stent, as discussed above. The splinting portion 80 serves as a splinting device for the nasal septum S or the medial wall 2.

Another embodiment of the invention is shown in FIG. 7 where the stent is formed with an opening 90 in the internal foam portion 60, between the ends 52, 54. The opening 90 is defined by a surface 95 that is minimally porous similar to the outer surfaces of the stent 10, and also may have substantial mechanical strength as the splinting portion 80 as shown in FIG. 6. This embodiment provides a stent 10 with more structural rigidity, which provides greater support when it is inserted into the nasal cavity.

All of the stents 10 described above can be formed as shown or they can be formed with a string or other type of tab included to assist in the removal from the nasal cavity. By utilizing the expandable, hydrophilic foam material described above with the minimally porous outer surface, the nasal cavity is held apart or open postoperatively in order to prevent the mucosal surfaces of the nasal cavity from scaring or adhering to each other. With the surfaces formed of a material that will not adhere to the mucosa, the stents allow for normal healing coupled with reduction of postoperative swelling by the light even pressure applied to the surfaces of the nasal cavity.

It should be understood that the invention as described above can be modified or improved without departing from the spirit and scope of the invention as defined in the appended claims, and such claims should not be limited but should also be construed to cover such modifications and improvements.

What is claimed is:

1. An expandable nasal stent for postoperative nasal packing, comprising:
   (a) a body having outer surfaces corresponding generally to the mucosal surfaces that define a human nasal cavity;
   (b) the body being formed of a unitary layer of inherently porous foam material capable of expanding outwardly, and having a nonadherent surface for absorbing fluids from the nasal cavity without adhering to the mucosal surfaces of the nasal cavity; and
   (c) the body being capable of providing a nasal stent for postoperative nasal packing so as to prevent adhesions and scar formation between the mucosal surfaces.

2. The nasal stent of claim 1, wherein the highly porous foam material is selected from a group consisting of medical grade polyurethane hydrophilic foams having a base material of polyether polyisocynate or other primary amines.

3. The nasal stent of claim 1, wherein the minimally porous outer surface has a thickness of 0.001–2 mm.

4. The nasal stent of claim 1, wherein the body and outer surface are chemically the same.

5. The nasal stent of claim 1, wherein the outer surface includes a non-porous portion for sufficient rigidity to form a splint.

6. The nasal stent of claim 5, wherein the non-porous portion is about 2 mm. thick and is chemically the same as the body.

7. The nasal stent of claim 1, wherein a trough is formed on the outer surface of the body allowing for the accommodation of a middle nasal turbinate on the lateral wall of a human nasal cavity.

8. The nasal stent of claim 7 wherein the trough includes a minimally porous outer surface.

9. The nasal stent of claim 1, and further including an opening extending through the expandable nasal stent from end to end.

10. The nasal stent of claim 9, wherein the surface of the body defining the opening is minimally porous.

* * * * *